United States Patent [19]

Schwamborn et al.

[11] Patent Number: 4,877,443
[45] Date of Patent: Oct. 31, 1989

[54] 2,4-DIAMINO-6-TRIFLUOROMETHYL-PYRIMIDINE COMPOUNDS USEFUL AS HERBICIDES

[75] Inventors: Michael Schwamborn, Cologne; Erich Klauke, Odenthal; Robert R. Schmidt, Bergisch-Gladbach; Hans-Joachim Santel, Leverkusen; Robert H. Strang, Duesseldorf, all of Fed. Rep. of Germany

[73] Assignee: Bayer Aktiengesellschaft, Leverkusen, Fed. Rep. of Germany

[21] Appl. No.: 2,881

[22] Filed: Jan. 13, 1987

[30] Foreign Application Priority Data

Jan. 22, 1986 [DE] Fed. Rep. of Germany ........ 3601800

[51] Int. Cl.$^4$ .................... C07D 239/48; A01N 43/54
[52] U.S. Cl. ........................................ 71/92; 544/323
[58] Field of Search .................... 544/323, 326, 330; 71/92

[56] References Cited

U.S. PATENT DOCUMENTS

| | | | |
|---|---|---|---|
| 3,284,188 | 11/1966 | Amagasa et al. | 544/323 |
| 4,025,515 | 5/1977 | Schneider | 544/323 |
| 4,116,674 | 9/1978 | Sunky et al. | 544/323 |

FOREIGN PATENT DOCUMENTS

| | | | |
|---|---|---|---|
| 0111440 | 10/1983 | European Pat. Off. | 546/323 |
| 2006145 | 10/1970 | Fed. Rep. of Germany | 544/323 |
| 2630140 | 1/1977 | Fed. Rep. of Germany | 544/323 |
| 0000681 | 2/1979 | Fed. Rep. of Germany | 544/323 |
| 3445293 | 6/1986 | Fed. Rep. of Germany | 544/323 |
| 89670 | 5/1984 | Japan | 544/323 |

OTHER PUBLICATIONS

Chem. Abstract, vol. 101:151874a, * p. 719, Oct. 22, 1984.

*Primary Examiner*—Richard A. Schwartz
*Assistant Examiner*—Zinna Northington
*Attorney, Agent, or Firm*—Sprung Horn Kramer & Woods

[57] ABSTRACT

Herbicidally active 2,4-diamino-6-haloalkylpyrimidines of the formula

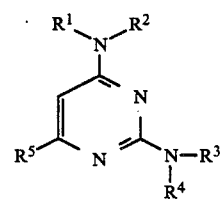

in which $R^1$ and $R^3$, independently of one another, represent hydrogen or alkyl, $R^2$ and $R^4$, independently of one another, represent hydrogen, alkyl which is optionally substituted by halogen, cyano, alkoxy, alkylthio or by cyclopropyl, represent cycloalkyl, alkenyl which is optionally substituted by halogen, or alkinyl, and $R^5$ represents alkyl which is substituted by halogen, with the proviso that $R^1$, $R^2$, $R^3$ and $R^4$ do not simultaneously represent hydrogen when $R^5$ represents trichloromethyl, and with the provisio that $R^1$ and $R^2$ do not simultaneously represent hydrogen when $R^4$ represents alkyl which is substituted by alkoxy or alkylthio.

10 Claims, No Drawings

2,4-DIAMINO-6-TRIFLUOROMETHYLPYRIMIDINE COMPOUNDS USEFUL AS HERBICIDES

The present invention relates to novel 2,4-diamino-6-haloalkylpyrimidines, processes and novel intermediates for their preparation, and also to their use as plant protection agents, particularly as herbicides.

It is already known that certain 2,4-diaminopyrimidines, for example 2,4-diamino-6-chloro-5-methylthiopyrimidine or 2-(3-methoxypropylamino)-4-cyclopropylamino-6-chloropyrimidine, can be employed as herbicides (cf. EP-A No. 0,000,681, DE-OS (German Published Specification) No. 2,006,145, DE-OS (German Published Specification) No. 2,630,140). However, their action when applied in small amounts is not satisfactory for various weeds.

Novel 2,4-diamino-6-haloalkyl-pyrimidines of the general formula (I)

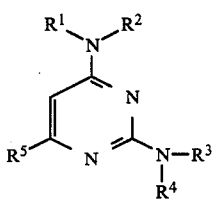

in which
$R^1$ and $R^3$, independently of one another, represent hydrogen or alkyl,
$R^2$ and $R^4$, independently of one another, represent hydrogen, alkyl which is optionally substituted by halogen, cyano, alkoxy, alkylthio or by cyclopropyl, represent cycloalkyl, alkenyl which is optionally substituted by halogen, or alkynyl,
$R^5$ represents alkyl which is substituted by halogen, with the proviso that $R^1$, $R^2$, $R^3$ and $R^4$ do not simultaneously represent hydrogen when $R^5$ represents trichloromethyl, and
with the proviso that $R^1$ and $R^2$ do not simultaneously represent hydrogen when $R^4$ represents alkyl which is substituted by alkoxy or alkylthio,
have been found.

It has furthermore been found that the 2,4-diamino-6-haloalkyl-pyrimidine derivatives of the general formula (I) are obtained when pyrimidines of the general formula (II)

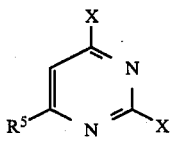

in which
$R^5$ has the abovementioned meaning and
X represents chlorine or fluorine,
are initially reacted with an amine of the formula (III)

in which $R^1$ and $R^2$ have the abovementioned meaning, if appropriate in the presence of an acid acceptor and if appropriate in the presence of a diluent, to form a mixture of the isomeric pyrimidine derivatives of the general formula (IVa) and (IVb) (1st stage)

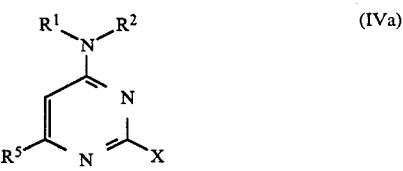

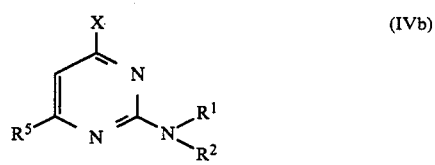

in which $R^1$, $R^2$, $R^5$ and X have the abovementioned meaning, and are subsequently, if appropriate after separation of the structurally isomeric pyrimidine derivatives of the formula (IVb), reacted, in a further reaction stage, with amines of the formula (V)

in which $R^3$ and $R^4$ have the abovementioned meaning, in the presence of an acid acceptor and if appropriate in the presence of a diluent, to form pyrimidine derivatives of the formula (I) (2nd stage).

In addition, it has been found that the novel 2,4-diamino-6-haloalkylpyrimidine derivatives of the general formula (I) display strong herbicidal properties.

The novel 2,4-diamino-6-haloalkylpyrimidine derivatives of the formula (I) according to the invention are distinguished structurally, compared to the previously known pyrimidines, in particular in that the 6 position is substituted by a haloalkyl group and the 5 position displays a hydrogen atom.

Surprisingly, the active compounds, according to the invention, of the formula (I) are markedly more active than the previously known pyrimidine derivatives, such as, for example, 2,4-diamino-6-chloro-5-methylthiopyrimidine (known from EP-A No. 0,000,681) or 2-(3-methoxypropylamino)-4-cyclopropylamino-6-chloropyrimidine (known from DE-OS (German Published Specification) No. 2,630,140), at the same time being more compatible with culture plants.

Amongst the 2,4-diamino-6-haloalkylpyrimidine derivatives, according to the invention, of the formula (I), those are preferred
in which
$R^1$ and $R^3$, independently of one another, represent hydrogen or alkyl having 1-6 C atoms,
$R^2$ and $R^4$, independently of one another, represent hydrogen, alkyl, having 1-8 C atoms, which is optionally substituted by fluorine, chlorine, bromine, iodine, cyano or cyclopropyl, represent alkoxyalkyl or alkylthioalkyl, in each case having 1-6 C atoms in each alkylthio or alkoxy moiety and 2-8 C atoms in each alkyl moiety, cycloalkyl having 3-5 C atoms, alkenyl, having 3-6 C atoms, which is optionally substituted by halogen, or alkynyl having 3-6 C atoms,
$R^5$ represents halomethyl, with the proviso that $R^1$, $R^2$, $R^3$ and $R^4$ do not simultaneously represent hydrogen when $R^5$ represents trichloromethyl, and with the proviso that $R^1$ and $R^2$ do not simultanously represent hydrogen when $R^4$ represents alkoxyalkyl or alkylthioalkyl, in each case having 1–6 C atoms in each alkylthio or alkoxy moiety and 2–8 C atoms in each alkyl moiety.

From this group of substances, those compounds of the formula (I) are particularly preferred in which $R^1$ and $R^3$, independently of one another, represent hydrogen or alkyl having 1–4 C atoms, $R^2$ and $R^4$, independently of one another, represent hydrogen, alkyl, having 1–6 C atoms, which is optionally substituted by fluorine, chlorine, cyano or cyclopropyl, represent alkoxyalkyl or alkylthioalkyl, in each case having 1–4 C atoms in each alkylthio or alkoxy moiety and 2–6 C atoms in each alkyl moiety, cyclopropyl or cyclobutyl, or alkenyl, having 3–5 C atoms, which is optionally substituted by chlorine, or alkinyl having 3–5 C atoms, and $R^5$ represents methyl which is substituted by chlorine and/or fluorine, with the proviso that $R^1$, $R^2$, $R^3$ and $R^4$ do not simultaneously represent hydrogen when $R^5$ represents trichloromethyl, and with the proviso that $R^1$ and $R^2$ do not simultaneously represent hydrogen when $R^4$ represents alkoxyalkyl or alkylthioalkyl, in each case having 1–4 C atoms in each alkylthio or alkoxy moiety and 2–6 C atoms in each alkyl moiety.

Very particularly preferred are pyrimidine derivatives of the formula (I) in which $R^1$ and $R^3$, independently of one another, represent hydrogen, methyl or ethyl and $R^2$, $R^4$ and $R^5$ have the meanings which are mentioned as being particularly preferred.

If, for example, 2,4-difluoro-6-trifluoromethylpyrimidine and cyclopropylamine are used as starting materials and the 4-cyclopropylamino-2-fluoro-6-trifluoromethylpyrimidine thereby formed is reacted with 3-methoxypropylamine, then the course of the reaction can be summarized by the following reaction scheme:

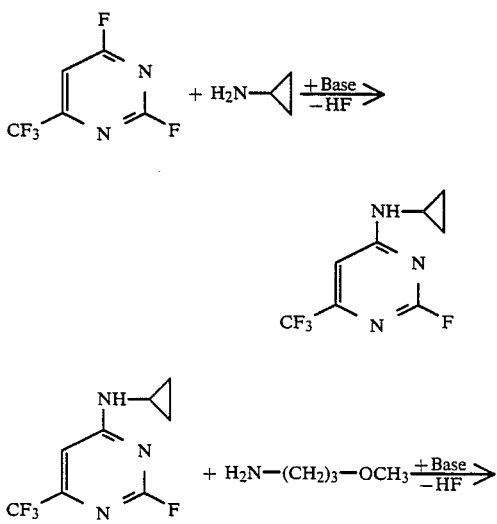

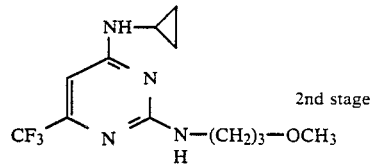

2nd stage

The pyrimidines which are used as starting materials are generally defined by the formula (II). In this formula, $R^5$ preferably or particularly preferably represents those radicals which have already been mentioned in the description of the substances, according to the invention, of the formula (I) as being preferred or particularly preferred for these substituents, and X represents chlorine or fluorine. Some of the pyrimidines of the formula (II) are known or can be prepared by known methods (cf. preparation examples of the starting materials).

The following compounds, in particular, can be employed as pyrimidine derivatives of the formula (II): 2,4-dichloro-6-trifluoromethylpyrimidine, 2,4-dichloro-6-difluorochloromethylpyrimidine, 2,4-dichloro-6-dichlorofluoromethylpyrimidine, 2,4-dichloro-6-trichloromethylpyrimidine, 2,4-difluoro-6-trifluoromethylpyrimidine, 2,4-difluoro-6-difluorochloromethylpyrimidine, 2,4-difluoro-6-dichlorofluoromethylpyrimidine and 2,4-difluoro-6-trichloromethylpyrimidine.

The amines which are furthermore used as starting materials are generally defined by the formulae (III) and (V). In these formulae, $R^1$, $R^2$, $R^3$ and $R^4$ preferably or particularly preferably represent those radicals which have already been mentioned in the description of the substances, according to the invention, of the formula (I) as being preferred or particularly preferred for these substituents. The amines of the formula (III) and (IV) are known or can be prepared by known methods in analogous fashion to the known compounds (cf., for example, Houben-Weyl, Methoden der organischen Chemie [Methods of Organic Chemistry], Volume XI/1, p. 548, p. 561 et seq., 4th edition 1957; U.S. Pat. No. 2,764,615).

In detail, the following amines of the formulae (III) or (V) can, in particular, be employed for the preparation of the pyrimidine derivatives of the general formula (I): methylamine, ethylamine, n-propylamine, i-propylamine, n-butylamine, s-butylamine, t-butylamine, neopentylamine, dimethylamine, diethylamine, di-n-propylamine, di-i-propylamine, 3-methoxypropylamine, 3-ethoxypropylamine, 3-n-propoxy-propylamine, 3-i-propoxypropylamine, 3-n-butoxypropylamine, 3-s-butoxypropylamine, 3-t-butoxypropylamine, 1-methyl-3-methoxy-propylamine, 1-methyl-3-ethoxypropylamine, 1-methyl-3-n-propoxypropylamine, 1-methyl-3-i-propoxypropylamine, 1-methyl-3-t-butoxypropylamine, 2-methoxyethylamine, 2-ethoxyethylamine, 2-n-propoxyethylamine, 2-i-propoxyethylamine, 2-n-butoxyethylamine, 2-s-butoxyethylamine, 2-t-butoxyethylamine, 1-Methyl-2-methoxyethylamin, 1-Methyl-3-ethoxyethylamin, N-methyl-N-3-methoxypropylamine, 3-methylthiopropylamine, allylamine, 1-methylallylamine, 1,1-dimethylallylamine, propargylamine, 1-methylpropargylamine, cyclopropylamine and cyclobutylamine.

Suitable diluents for the process according to the invention are organic solvents and water. Preferred organic solvents are hydrocarbons such as toluene, aliphatic ketones such as acetone, methyl ethyl ketone and diethyl ketone, and cycloaliphatic ethers such as tetrahydrofuran or dioxane. Mixtures of different organic solvents and mixtures of water-miscible organic solvents with water are also suitable as diluents.

The process according to the invention is, if appropriate, carried out using acid binders. As such, alkaline earth metal and alkali metal hydroxides, such as calcium hydroxide, sodium hydroxide or potassium hydroxide, furthermore ammonia and also tertiary aliphatic amines, such as, for example, triethylamine, but also amine starting compound (III) or (V) employed in excess are particularly suitable.

The reaction temperatures can be varied within a relatively wide range in the process according to the invention. The first process stage is, in general, carried out at temperatures from $-80°$ C. to $+150°$ C., preferably from $-80°$ C. to $+20°$ C. The second process stage is, in general, carried out at temperatures from $-80°$ C. to $250°$ C., preferably from $-20°$ C. to $+150°$ C.

The reaction is carried out in the pressure range from 1 to about 10 bar.

In the first stage, 1 to 2 mols, preferably 1 to 1.1 mols, of amine of the formula (III) and 1 to 2 mols, preferably 1 to 1.2 mols, of acid acceptor are, in general, employed per mol of pyrimidine of the formula (II) when the process according to the invention is carried out, the amine of the formula (III) being optionally used as acid binder. The first stage is particularly preferably carried out using stoichiometrical molar ratios. The same goes for the second process stage.

Structurally isomeric pyrimidine by-products of the formula (IVb) which are possibly produced in the first stage of the process can be separated off in a simple fashion by known methods, particularly by recrystallization, chromatography or steam distillation (cf., for example, DE-OS (German Published Specification) No. 2,006,145, DE-OS (German Published Specification) No. 2,630,140, European Patent Specification No. 0,114,575), so that the pyrimidine derivatives of the formula (IVa) can be isolated in an adequately pure form.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and in paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used—in particular by the post-emergence method—for the selective combating of weeds in monocotyledon cultures, e.g. corn, rice, barley and wheat, and in dicotyledon cultures, e.g. in cotton. In the post-emergence method, the active compounds according to the invention can be used, in particular, against dicotyledon crops.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Known herbicides, such as, for example, 1-amino-6-ethylthio-3-(2,2-dimethylpropyl)-1,3,5-triazine-2,4(1H, 3H)-dione or N-(2-benzothiazolyl)-N,N'-dimethylurea for combating weeds in cereals; 4-amino-3-methyl-6-phenyl-1,2,4-triazin-5(4H)-one for combating weeds in sugar beet, and 4-amino-6-(1,1-dimethylethyl)-3-methylthio-1,2,4-triazin-5(4H)-one for combating weeds in soy beans, are suitable for the mixtures.

Mixtures with ureas, such as N-benzothiazolyl-N-methyl-N'-methylurea; N,N-dimethyl-N'-(3-chloro-4-methylphenyl)-urea; N,N-dimethyl-N'-(4-isopropylphenyl)-urea; N,N-dimethyl-N'-(3-trifluoromethylphenyl)-urea; triazines, such as 2-chloro-N-{{(4-methoxy-6-methyl-1,3,5-triazin-2-yl)-amino}-carbonyl}-benzenesulphonamide; 2-chloro-4-ethylamino-6-isopropylamino-1,3,5-triazine; 2-chloro-4-ethylamino-6-(3-cyanopropylamino)-1,3,5-triazine; 2-chloro-4,6-bis-(ethylamino)-1,3,5-triazine; 4-ethylamino-2-t-butylamino-6-methylthio-s-triazine; triazinones, such as 4-amino-6-tert.-butyl-3-methylthio-4,5-dihydro-1,2,4-triazin-5-one; 3-methyl-4-amino-6-phenyl-1,2,4-triazin-5-(4H)-one; triazinediones; nitroanilines, such as N-(3,4-dichlorophenyl)-2-propionamide, 2,6-dinitro-4-trifluoromethyl-N,N-dipropylaniline; N-(1-ethylpropyl)-3,4-dimethyl-2,6-dinitroaniline; oxyacetamides, such as N-methyl-2-(1,3-benzthiazol-2-yloxy)-acetanilide; chloroacetanilides, such as N-(methoxymethyl)-2,6-diethyl-chloroacetanilide, 2-ethyl-6-methyl-N-(1-methyl-2-methoxyethyl)-chloroacetanilide, α-chloro-2',6'-diethyl-N-(2-propoxyethyl)-acetanilide; thiolcarbamates, such as N,N-diisopropyl-S-(2,3,3-trichloroallyl)-thiolcarbamate, benzyl ether; phenoxyalkanecarboxylic acids, such as 2,4-dichlorophenoxyacetic acid; 2,4-dichlorophenoxypropionic acid, (2-methyl-4-chlorophenoxy)-acetic acid, (4-chloro-2-methylphenoxy)propionic acid; aryloxy- or heteroaryloxyphenoxyalkanecarboxylic acids, such as methyl 2-{4-(2,4-dichlorophenoxy)-phenoxy}-propionate, 2-{4-[[3-chloro-5-(trifluoromethyl)-2-pyridinyl]-oxy]-phenoxy}-propanoic acid or the ethyl ester thereof, trimethylsilyl-methyl 2-[4-(3,5-dichloropyrid-2-yl-oxy)-phenoxy]-propionate; cyclohexanediones, such as methyl 6,6-dimethyl-2,4-dioxo-3-[1-(2-propenyloxyamino)-butylidene]-cyclohexanecarboxylic acid, 2-[1-(ethoxyaminobutylidene]-5-(2-ethylthiopropyl)-1,3-cyclohexanedione; benzonitriles, such as 3,5-diiodo-4-hydroxybenzonitrile; 3,5-dibromo-4-hydroxybenzonitrile; 3-isopropyl-2,1,3-benzothiadiazin-4-one 2,2-dioxide; 6-chloro-3-phenyl-pyridazin-4-yl S-octyl-thiocarbonate; pyridyloxyacetic acids, pyridones, such as 1-methyl-3-phenyl-5-[3-(trifluoromethyl)-phenyl]-4(1H)-pyridinone, pyrazoles, such as [4-(2,4-dichlorobenzoyl)-1,3-dimethylpyrazol-5-yl]-4-methylphenylsulphonate, are also suitable. Surprisingly, some mixtures also exhibit a synergistic effect.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

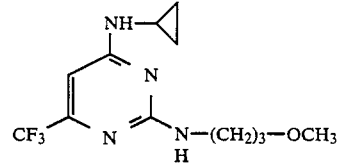

4-Cyclopropylamino-2-(3-methoxypropylamino)-6-trifluoromethylpyrimidine (a) 4-Cyclopropylamino-2-fluoro-6-trifluoromethylpyrimidine (1st stage)

2.9 g (0.05 mol) of cyclopropylamine and 5 g (0.05 mol) of triethylamine are added dropwise at −78° C. to 9.2 g (0.05 mol) of 2,4-difluoro-6-trifluoromethylpyrimidine in 200 ml of tetrahydrofuran. The reaction mixture is warmed slowly to −20° C., stirred for 2 hours at this temperature and subsequently stirred for 30 minutes at −10° C.

After mixing with 1 l of ice-water and extracting with dichloromethane, the combined organic phases are dried and concentrated. After addition of 50 ml of pentane, filtering off with suction and drying, 7.5 g (67.8% of theory) of the desired pyrimidine are obtained. M.p.: 79°-80° C.

(b) 4-Cyclopropylamino-2-(3-methoxypropylamino)-6-trifluoromethylpyrimidine (2nd stage)

6.1 g (0.068 mol) of 3-methoxypropylamine are added dropwise at room temperature to 7 g (0.0031 mol) of 4-cyclopropylamino-2-fluoro-6-trifluoromethylpyrimidine dissolved in 100 ml of tetrahydrofuran, and the mixture is stirred for 6 hours at room temperature. After addition of 2 l of ice-water, extraction with dichloromethane, drying of the organic phase and concentrating, 8.8 g (95.4% of theory) of the desired pyrimidine are obtained.

$n_D^{20}$: 1.5040

The pyrimidine derivatives, of the general formula (I)

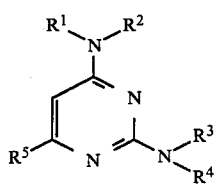

mentioned in Table 1 below can be prepared by analogous routes:

TABLE 1

| Example No. | $R^1$ | $R^2$ | $R^3$ | $R^4$ | $R^5$ | Physical constants |
|---|---|---|---|---|---|---|
| 2 | H | ◁ | H | —C(CH₃)₂—CH₂—OCH₃ | —CF₃ | M.p.: 74° C. |
| 3 | H | —C₃H₇—n | H | —(CH₂)₃—OCH₃ | —CF₃ | $n_D^{20}$: 1.4990 |
| 4 | H | —C₄H₉—t | H | —(CH₂)₃—OCH₃ | —CF₃ | M.p.: 93° C. |
| 5 | H | —C₂H₅ | H | —C₃H₇—i | —CF₃ | $n_D^{20}$: 1.4989 |
| 6 | H | —C₂H₅ | H | —(CH₂)₃—OCH₃ | —CF₃ | $n_D^{20}$: 1.5024 |
| 7 | H | —C₃H₇—i | H | —C₂H₅ | —CF₃ | M.p.: 57° C. |
| 8 | H | —C₃H₇—i | H | —(CH₂)₃—OCH₃ | —CF₃ | M.p.: 67° C. |
| 9 | H | ◁ | H | —(CH₂)₃—OCH₃ | —CCl₂F | $n_D^{20}$: 1.5555 |
| 10 | H | ◁ | H | —(CH₂)₃—OCH₃ | —CClF₂ | $n_D^{20}$: 1.5232 |
| 11 | H | —C₃H₇—i | H | —(CH₂)₃—OCH₃ | —CClF₂ | $n_D^{20}$: 1.5170 |
| 12 | H | —CH₃ | H | —(CH₂)₃—OCH₃ | CF₃ | $n_D^{20}$: 1.5040 |

STARTING MATERIALS

The pyrimidine derivatives, of the formula (II-1) to (II-4) which are used as starting materials are known or can be obtained in analogous fashion by processes described in the following references:

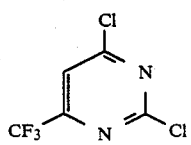

(II-1): known from:
H. Gershon et al.
J. Heterocyclic Chem. 20, 219 (1983)

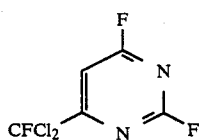

(II-2): known from:
DE-OS (German Published Specification) 3,118,699

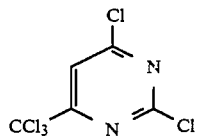

(II-3): known from:
DE-OS (German Published Specification) 3,118,699

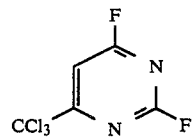

(II-4): known from:
DE-OS (German Published Specification) 3,118,699

The pyrimidine derivatives (II-5) to (II-8) which have not previously been described can be obtained as follows:

EXAMPLE II-5

2,4-Difluoro-6-chlorodifluoromethylpyrimidine

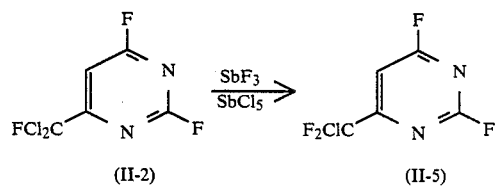

104 g of 2,4-difluoro-6-dichlorofluoromethylpyrimidine, 26 g of antimony trifluoride and 2.4 g of antimony pentachloride are initially introduced in a stirred apparatus and stirred under reflux for 1 hour at a temperature of 154°-149° C. The reaction product is distilled off in vacuo, washed with dilute hydrochloric acid and dried. After redistillation, 2,4-difluoro-6-chlorodifluoromethyl-pyrimidine of boiling point b.p.: 137°-139° C., $n_D^{20}$: 1.4213, is obtained.

EXAMPLE II-6

2,4-Difluoro-6-trifluoromethyl-pyrimidine

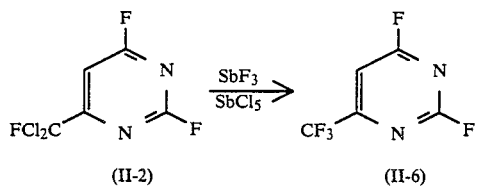

252 g of 2,4-difluoro-6-dichlorofluoromethylpyrimidine, 209 g of antimony trifluoride and 105 g of antimony pentachloride are initially introduced in a stirred apparatus and stirred under reflux for 15 minutes at a temperature of 130°–120° C. The reaction product is distilled off under a slight vacuum, washed with dilute hydrochloric acid, and dried. After redistillation, 2,4-difluoro-6-trifluoromethyl-pyrimidine of boiling point b.p.: 108°–109° C., $n_D^{20}$: 1.3799, and also 2,4-difluoro-6-difluorochloromethylpyrimidine (Example II-5), are obtained.

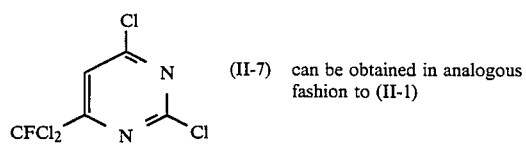

(II-7) can be obtained in analogous fashion to (II-1)

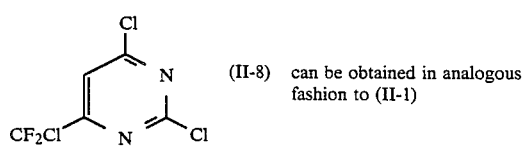

(II-8) can be obtained in analogous fashion to (II-1)

USE EXAMPLES

In the following use examples, the compounds listed below were used as comparison substances:

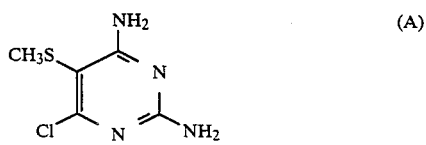

(known from EP-A-No.0,000,681, Example 16).

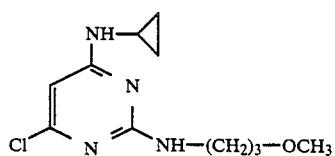

(known from DE-OS (German Published Specification) No. 2,630,140, Example 33).

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:
0% = no action (like untreated control)
100% = total destruction In this test, the compound according to Preparation Example 1, for example, displays a herbicidal action against mono- and dicotyledon weed plants, such as Chenopodium, Datura, Stellaria, Setaria and Panicum, which is clearly superior to the comparison substance (A), with the same culture plant compatibility in cotton.

In this test, the compound according to Preparation Example 1, for example, displays a herbicidal action against mono- and dicotyledon weeds, such as Datura, Matricaria, Cynodon or Setaria, which is clearly better than that of the comparison substance (B), besides a very good culture plant compatibility in cotton, rice and, in particular, in corn.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:
0% = no action (like untreated control)
100% = total destruction In this test, the compound according to Preparation Example (1), for example, displays a better culture plant compatibility in cotton and corn, particularly in cotton, and a clear superiority in the herbicidal action against mono- and dicotyledon weeds, such as Amaranthus, Chenopodium, Galium, Portulaca, Solanum, Echinochloa and Poa, compared with the comparison substance (A).

In this test, the compound according to Preparation Example (1), for example, displays a clearly better culture plant compatibility in monocotyledon (such as rice, barley and wheat) and dicotyledon cultures (such as cotton) and a clearly better herbicidal action against mono- and dicotyledon weeds (such as Abutilon, Galium, Helianthus or Ipomoea), than the comparison substance (B).

It will be appreciated that the instant specification and examples are set forth by way of illustration and not limitation, and that various modifications and changes may be made without departing from the spirit and scope of the present invention.

We claim:

1. A 2,4-diamino-6-haloalkylpyrimidine of the formula

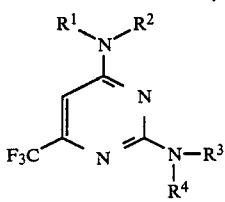

in which
R¹ and R³, independently of one another, represent hydrogen or alkyl having 1–6 C atoms, and
R² and R⁴, independently of one another, represent hydrogen, alkyl having 1–8 C atoms, which is unsubstituted or substituted by fluorine, chlorine, bromine, iodine, cyano or cyclopropyl, represent alkoxyalkyl or alkylthioalkyl, in each case having 1–6 C atoms in each alkylthio or alkoxy moiety and 2–8 C atoms in each alkyl moiety, cycloalkyl ahving 3–5 C atoms, alkenyl, having 3–6 C atoms, which is unsubstituted or substituted by halogen, or alkynyl having 3–6 C atoms, and with the provisos that (a) R³ and R⁴ do not simultaneously represent hydrogen, and (b) R¹ and R² do not simultaneously represent hydrogen when R⁴ represents alkoxyalkyl or alkylthioalkyl.

2. A 2,4-diamino-6-haloalkylpyrimidine according to claim 1, in which
R¹ and R³, independently of one another, represent hydrogen or alkyl having 1–4 C atoms, and
R² and R⁴, independently of one another, represent hydrogen, alkyl having 1–6 C atoms, which is unsubstituted or substituted by fluorine, chlorine, cyano or cyclopropyl, alkoxyalkyl or alkylthioalkyl, in each case having 1–4 C atoms in each alkylthio or alkoxy moiety and 2–6 C atoms in each alkyl moiety, cyclopropyl or cyclobutyl, or alkenyl, having 3–5 C atoms, which is unsubstituted or substituted by chlorine, or alkynyl having 3–5 C atoms, and
R⁵ represents methyl which is substituted by chlorine and/or fluorine, with the provisos that (a) R³ and R⁴ do not simultaneously represent hydrogen, and (b) R¹ and R² do not simultaneously represent hydrogen when R⁴ represents alkoxyalkyl or alkylthioalkyl.

3. A compound according to claim 1, wherein such compound is 4-cyclopropylamino-2-(3-methoxypropylamino)-6-trifluoromethylpyrimidine of the formula

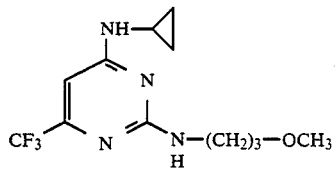

4. A compound according to claim 1, wherein such compound is 4-ethylamino-2-(3-methoxypropylamino)-6-trifluoromethylpyrimidine of the formula

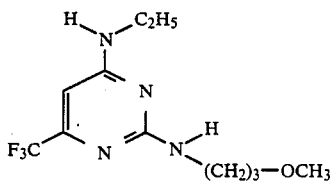

5. A compound according to claim 1, wherein such compound is 4-isopropylamino-2-ethylamino-6-trifluoromethylpyrimidine of the formula

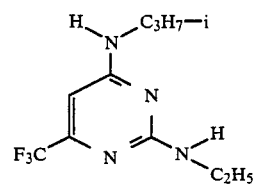

6. A compound according to claim 1, wherein such compound is 4-isopropylamino-2-(3-methoxypropylamino)-6-trifluoromethylpyrimidine of the formula

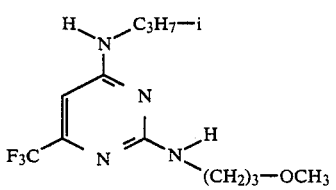

7. A herbicidal composition comprising a herbicidally effective amount of a compound according to claim 1 and a diluent.

8. A method of combating unwanted vegetation which comprises applying to such vegetation or to a locus from which it is desired to exclude such vegetation a herbicidally effective amount of a compound according to claim 1.

9. The method according to claim 8, wherein such compound is
4-cyclopropylamino-2-(3-methoxypropylamine)-6-trifluoromethylpyrimidine,
4-ethylamino-2-(3-methoxypropylamino)-6-trifluoromethylpyrimidine,
4-isopropylamino-2-ethylamino-6-trifluoromethylpyrimidine, or
4-isopropylamino-2-(3-methoxypropylamino)-6-trifluoromethylpyrimidine.

10. A 2,4-diamino-6-haloalkylpyrimidine according to claim 1, in which
R¹ is alkyl having 1–6 C atoms.